United States Patent [19]
Van Ness et al.

[11] Patent Number: 4,670,589
[45] Date of Patent: Jun. 2, 1987

[54] PREPARATION OF N-ACETYL-P-AMINOPHENOL

[75] Inventors: John H. Van Ness, Des Peres; J. Bruce Warner, Maryland Heights, both of Mo.

[73] Assignee: Monsanto Company, St. Louis, Mo.

[21] Appl. No.: 671,057

[22] Filed: Nov. 13, 1984

Related U.S. Application Data

[63] Continuation of Ser. No. 439,244, Nov. 4, 1982, abandoned.

[51] Int. Cl.$^4$ .................................................. C07C 103/10
[52] U.S. Cl. .................................... 564/144; 564/418
[58] Field of Search ........................ 564/144, 418

[56] References Cited

U.S. PATENT DOCUMENTS

| | | |
|---|---|---|
| 2,947,781 | 8/1960 | Spiegler .......................... 564/418 X |
| 3,076,030 | 1/1963 | Freifelder .......................... 564/144 |
| 3,079,435 | 2/1963 | Freifelder et al. .................. 564/144 |
| 3,341,587 | 9/1967 | Duesel .................... 564/144 |
| 3,694,508 | 9/1972 | Baron et al. ........................ 564/418 X |
| 3,717,680 | 2/1973 | Baron et al. ........................ 564/144 X |
| 3,845,129 | 10/1974 | Reid ............................... 564/418 X |
| 3,917,695 | 11/1975 | Schulman et al. .................. 564/144 |
| 4,264,525 | 4/1981 | Huber ................................ 564/223 |

*Primary Examiner*—Robert V. Hines
*Attorney, Agent, or Firm*—Jon H. Beusen; Thomas E. Kelley; Wendell W. Brooks

[57] ABSTRACT

Production of N-acetyl-p-aminophenol by hydrogenation of p-nitrophenol to p-aminophenol and concurrently acetylating the p-aminophenol with acetic anhydride with the acetylation controlled so that substantially no excess acetic anhydride is present in the system until the hydrogenation reaction has reached substantial completion.

12 Claims, No Drawings

PREPARATION OF N-ACETYL-P-AMINOPHENOL

This is a continuation of application Ser. No. 439,244, filed Nov. 4, 1982, and now abandoned.

BACKGROUND OF THE INVENTION

1. Field of the Invention

This invention relates to the production of N-acetyl-p-aminophenol by hydrogenation of p-nitrophenol to p-aminophenol, and concurrently acetylating the p-aminophenol with acetic anhydride.

2. Background

The conventional process for the production of N-acetyl-p-aminophenol involves reduction of p-nitrophenol to produce p-aminophenol which is then acetylated to produce N-acetyl-p-aminophenol. The reduction of p-nitrophenol to produce p-aminophenol involves hydrogenating the p-nitrophenol in the presence of catalysts such as aluminum. platinum, palladium, noble metal catallysts, oxides of platinum, palladium or noble metal catalysts, molybdenum sulfide, and platinum sulfide. Gaseous hydrogen is commonly used as a reducing agent. The acetylating agent is usually acetic anhydride. The reaction medium can be acetic acid water, a water-isopropanol mixture, or other inert medium.

This series of reactions has been carried on simultaneously as in U.S. Pat. No. 076.030 and U.S. Pat. No. 3,341,587. In both of these simultaneous reaction patents, p-nitrophenol and acetic anhydride are added at the beginning of the reaction sequence, and the hydrogenation of the p-nitrophenol takes place in the presence of acetic anhydride that is in excess over the amount of p-aminophenol in the system at any given moment. This reaction sequence has also been carried on in a step-wise manner in which the hydrogeantion of p-nitrophenol is completed prior to the acetylation step. This step-wise reaction scheme has been further refined in U.S. Pat. No. 4,264,525 which the hydrogenation step is interrupted and acetylation accompished followed by at least one further hydrogenation step each of which is followed by another acetylation step. all the while keeping the pH below about 7.0.

Because of its use as an analgesic, N-acetyl-p-aminophenol must be very pure and must not be colored. This invention produces N-acetyl-p-aminophenol that is less colored than that produced by prior art processes. Additionally, this invention produces N-acetyl-p-aminophenol in a shorter reaction time than prior art processes.

SUMMARY OF THE INVENTION

This invention provides a process for producing N-acetyl-p-aminophenol, comprising:

A. Hydrogenating p-nitrophenol to p-aminophenol; and

B. Concurrently acetylating the p-aminophenol to N-acetyl-p-aminophenol with acetic anhydride, with the rate of the acetylation reaction controlled so that substantially no excess acetic anhydride is present until the hyrodgention reaction has reached substantial completion.

DESCRIPTION OF THE PREFERRED EMBODIMENT

The first step in this series of reactions is the production of p-aminophenol by hydrogenation of p-nitrophenol. This reaction can take place in an autoclave or any other suitable hydrogenation equipment in the presence of a hydrogenation catalyst. A particularly preferred catalyst is wet palladium on carbon. The source of hydrogen for the hydrogenation reaction can be any gas containing sufficient hydrogen for hydrogenation. Although any gas mixture with sufficient partial pressure of hydrogen can be used. particularly preferred are hydrogen at a pressure of about 50-50 psig, (about 450-1140 kPa), and ammonia synthesis gas at a pressure of about 125-400 psig (about 965-2865 kPa).

The reaction medium may be either an aqueous solution or an aqueous-alcohol solution, such as isopropyl alcohol.

Once the hydrogenation reaction has started, addition of acetic anhydride can be begun. The rate of addition of acetic anhydride must be controlled so that substantially no excess acetic anhydride is present in the reaction system until the hydrogenation reaction has reached substantial completion. For purposes of controlling the addition of acetic anhydride, the hydrogenation reaction is considered to have reached substantial completion when the hydrogenation reaction has reached at least about 80% completion, preferably at least about 90% completion. Acetic anhydride is present in excess when the molar concentration of unreacted acetic anhydride is greater than the molar concentration of unreacted p-aminophenol at any given time. An overall excess of total acetic anhydride charged with respect to the total p-nitrophenol charged to the system can be used, however little advantage can be realized from using more than about 20% overall excess. As used herein, the phrase "overall excess" refers to the total amount of acetic anhydride added to the system over the entire sequence compared to the amount of p-nitrophenol starting material. Any other reference to an excess of acetic anhydride refers to the amount of unreacted acetic anhydride compared to the amount of unreacted p-aminophenol present in the system at any given time.

If the reaction conditions are controlled so that the reaction is run isothermally and under constant pressure, the rate of hydrogenation is essentially linear, so that the rate of addition of acetic anhydride can also be essentially linear. To simplfy control of the addition of acetic anhydride, and to help insure that acetic anhydride will not be in excess in the system, it is preferred that the hydrogenation be at least about 5% complete or preferably about 20% complete or more preferably about 30% complete before the addition of acetic anhydride is started. In order to obtain maximum benefits from this invention, addition of acetic anhydride should be begun before the hydrogenation reaction has reached about 35% completion however, acetylation can also be begun later in the reaction sequence.

The reaction sequence can be run at a temperature such that the hydrogenation reaction proceeds at a convenient rate. Preferably a temperature between about 50° C. and about 150° C. can be used and more preferably between about 90° C. and about 125° C.

The concentration of p-nitrophenol in the reaction mixture at the time the hydrogenation reaction is started can be as much as 75-80%, compared to 45-50% commonly used in prior art processes. It is not possible to operate a sequential reaction system with p-nitrophenol concentrations as high as 75–80% because the p-aminophenol produced exceeds its limit of solubility in the reaction mixture. The p-aminophenol can then become coated on the surfaces inside the reactor and on heat exchange surfaces, adversely affecting the performance of the system. Because this invention consumes the p-aminophenol at a rate close to its rate of production, p-aminophenol remains in solution, and the problems outlined above do not occur, even using initial p-nitrophenol concentrations as high as 75 to 80%. As a result, the payload for a given reactor system can be increased by using this invention.

The process of this invention has 3 major advantages over prior art processes. The process of this invention requires a shorter reaction time, results in higher payloads for a given size of equipment, and results in improved quality of N-acetyl-p-aminophenol.

The following Examples are intended to illlustrate this invention, and are not intended to in any way limit its scope. All parts and percentages are by weight, unless otherwise noted.

The N-acetyl-p-aminophenol produced in each of the Examples was subjected to the following color test procedure. Twenty grams of N-acetyl-p-aminophenol and 20 mililiters of methanol were placed in a beaker and stirred for three minutes. The solvents in the beaker were allowed to settle, and the supernatant liquid was centrifuged for about 4 minutes at greater than 3000 revolutions per minute. The absorbance of the clear supernatant liquid was measured at 420 nanometers in one cm cell. This absorbance is reported as color value. A higher color value indicates a more highly colored, less desirable product. A common limit of color value is an absorbance of 0.03, or more preferably 0.025.

In the following Examples, N-acetyl-p-aminophenol was produced using various processes both within and outside of the scope of this invention. Comparative Examples A through E utilize a two-step process outside the scope of this invention in which hydrogenation is completed prior to commencement of acetylation. Examples 1 through 8 use a coreaction system within the scope of this invention, in which acetic anhydride addition is begun during hydrogenation, but with acetic anhydride addition controlled so that no excess acetic anhydride exists in the system until the hydrogenation reaction is substantially completed. Comparative Exampes F and G use a coreaction system outside the scope of this invention, in which the acetic anhydride is added at a rate such that an excess of acetic anhydride over p-aminophenol exists in the system.

COMPARATIVE EXAMPLE A

Comparative Example A utilizes a two-step process outside the scope of this invention. About 220 g of p-nitrophenol about 80 g of isopropanol, and about 140 g of water were added to a high pressure autoclave, along with 3% palladium on carbon such that the dry weight of catalyst is equal to about 0.1% by weight of the p-nitrophenol. This resulted in a p-nitrophenol concentration of about 50%. The autoclave was purged of oxygen, pressurized to 70 psig with hydrogen, and was mildly agitated while being externally heated to 50° C. At 50° C. the agitation was increased and external heating was terminated. This was considered to be time equal to 0 minutes. The reaction temperature was allowed to rise to 106° C. and controlled at this temperature. The hydrogenation continued until the uptake of hydrogen stopped, about 57 minutes. The reaction mass was held at 100° C. and at 70 psig of hydrogen for 30 minutes. About 170 g of acetic anhydride was added continuously to the reaction mixture in approximately 14 minutes, while the reaction mass cooled to 95° C. The reactor contents were then held for about 37 minutes at 95° C. and 70 psig of hydrogen. The reaction mixture was filtered to remove the catalyst and was evaporatively cooled to about 40° C. During evaporative cooling, about 195 ml of distillate was collected, and was replaced with about 175 ml of water. The solution was then further cooled to 10° C. in an ice water bath. The slurry was filtered, and the wet solids were then reslurried in about 380 ml of demineralized water, stirred for about one hour and filtered again, to recover the solids. A yield of 87.5% based on p-nitrophenol was realized and the color value was 0.043.

COMPARATIVE EXAMPLE B

Comparative Example B used the same procedure as Comparative A except that about 155 g of water and about 65 g of isopropanol were charged to the autoclave. The hydrogenation temperature was 118° C. and the post-acetylation hold time was about 95 minutes. Also, the distillate removed in the evaporative cooling step was returned to the reaction mixture. This Example resulted in a hydrogenation time of 56 minutes, a yield of 80% and a color value of 0.029.

COMPARATIVE EXAMPLE C

Comparative Example C used the same procedure as Comparative Example A, except that the hydrogenation temperature was about 125° C., the post-acetylation hold time was about 40 minutes, and the distillate collected during evaporative cooling was returned to the reaction mixture. This Example resulted in a hydrogenation time of 51 minutes, a yield of 81% and a color value of 0.022.

COMPARATIVE EXAMPLE D

Comparative Example D used the same procedure as Comparative Example A, except that the hydrogenation temperature was about 125° C., the acetic anhydride charge was about 180 g, the post-acetylation hold time was 45 minutes, and the distillate collected during evaporative cooling was returned to the reaction mixture. This Example resulted in hydrogenation time of 62 minutes, a yield of 79% and a color value of 0.022.

COMPARATIVE EXAMPLE E

Comparative Example E used the same procedure as Comparative Example A except that about 245 g of p-nitrophenol, about 90 g of isopropanol, and about 110 g of water were charged to the autoclave, giving a p-nitrophenol concentration of about 55%. The hydrogenation temperature was 125° C. and the post-acetylation hold time was about 36 minutes. The amount of acetic anhydride charge was adjusted to maintain the same proportion with respect to p-nitrophenol as in Example A. During evaporative cooling about 215 ml of distillate was collected and replaced with 200 ml of demineralized water. This Example resulted in a hydrogenation time of about 56 minutes, a yield of 85%, and a color value of 0.033.

EXAMPLE 1

Example 1 utilizes a process within the scope of this invention. About 220 g of p-nitrophenol, about 80 g of isopropanol, and about 140 g of water were added to a high pressure autoclave, along with a 3% palladium on carbon catalyst such that the dry weight of catalyst is equal to about 0.05% by weight of the p-nitrophenol. This resulted in a p-nitrophenol concentration of about 50%. The autoclave was purged of oxygen, pressurized to 70 psig with hydrogen, and was mildly agitated while being externaly heated to about 50° C. At about 50° C., the agitation was increased and external heating was terminated. This was considered to be time equal to 0 minutes. The reaction temperature was allowed to rise to 110° C. and was controlled at this temperature. After about 20 minutes, the addition of acetic anhydride to the autoclave was begun. The molar rate of addition of the acetic anhydride was approximately equal to the molar rate of hydrogenation of p-nitrophenol to insure that no excess acetic anhydride would exist in the reaction mixture until the hydrogenation reaction had reached substantial completion. A total of 171 g of acetic anhydride was added. The hydrogenation continued until the uptake of hydrogen stopped, about 61 minutes, which means acetic anhydride addition was begun when the hydrogenation reaction was about 33% complete. the acetic anhydride feed continued about 14 minutes after the hydrogenation was completed. The reaction mass was then held at 110° C. and under a hydrogen pressure of 70 psig for about 200 minutes. The reaction mass was then filtered to remove the catalyst and was evaporatively cooled to about 40° C. During evaporative cooling about 240 ml of distillate was collected and was replaced with about 240 ml of water. The solution was then further cooled to 10° C. in an ice water bath. The slurry was filtered and the wet solids were then reslurried in about 380 ml of demineralized water, stirred for about one hour, and filtered to remove the solids. The yield of 89.5%, based on p-nitrophenol, was obtained and the color value was 0.013

EXAMPLE 2

Example 2 used the same procedure as Example 1 except that a 0.1% catalyst loading was used. Acetic anhydride addition was started at about 22 minutes, and continued for about 46 minutes. About 180 g of acetic anhydride was added totally. A 53 minute post-acetylation hold time as used, and the distillate removed during cooling was returned to the reaction mixture. This Example resulted in a hydrogenation time of about 50 minutes, a yield of about 81%, and a color value of 0.018. The acetic anhydride addition was begun at about 44% completion of the hydrogenation reaction.

EXAMPLE 3

Example 3 used the same procedure as Example 1 except that 0.1% catalyst loading was used. The acetic anhydride addition was begun after about 8 minutes. About 180 grams of acetic anhydride was added over a 59 minute addition time. A post-acetylation hold time of about 53 minutes was used. This Example resulted in a hydrogenation time of about 50 minutes, a yield of about 90%, and a color value of 0.013. The acetic anhydride addition was begun at about 16% completion of the hydrogenation reaction.

EXAMPLE 4

Example 4 used the same procedure as Example 1 except that a 0.1% catalyst loading was used. The acetic anhydride addition was started after about 38 minutes. A total of about 180 g acetic anhydride was added over about a 50 minute addition time. The post-acetylate hold time was about 56 minutes. This Example resulted in a hydrogenation time of about 51 minutes, a yield of 88%, and a color value of 0.020. The acetic anhydride addition was begun at about 75% completion of hydrogenation reaction.

EXAMPLE 5

Example 5 used the same procedure as Example 1 except that about 265 g of p-nitrophenol, and about 180 g of water and no isopropanol were charged to the autoclave, resulting in about a 60% p-nitrophenol concentration. A 0.1% catalyst loading was also used. The acetic anhdyride addition began after about 29 minutes. A total of 214 g of acetic anhydride was added over a 65 minute addition time. The post-acetylation hold time was about 52 minutes and the distillate collected during evaporative cooling was returned to the reaction mixture. This Example resulted in a hydrogenation time of about 80 minutes, a yield of about 88%, and a color value of 0.006. The addition of acetic anhydride was begun at about 36% completion of the hydrogenation reaction.

EXAMPLE 6

Example 6 used the same procedure as Example 1 except that about 200 g p-nitrophenol, about 170 g water and about 75 g isopropanol were charged to the autoclave, resulting in about a 45% p-nitrophenol concentration. The acetic anhydride addition was started after about 10 minutes. A total of 161 g of acetic anhydride was added over about a 34 minute addition time. The post-acetylation hold time was about 52 minutes, and the distillate collected during evaporative cooling was returned to the reaction mixture. This Example resulted in a hydrogenation time of about 31 minutes, a yield of about 79%, and a color of 0.003. The addition of acetic anhydride was begun at about 32% completion of the hydrogenation reaction.

Example 7

Example 7 used the same procedure as Example 1 except that about 265 g of p-nitrophenol were charged to the autoclave, resulting in about a 60% p-nitrophenol concentration. A 0.05% catalyst loading was also used. The acetic anhydride addition began after about 20 minutes. A total of about 200 g of acetic anhydride was added over a 61 minute addition time. The postacetylation hold time was about 62 minutes and the reaction mass was cooled without evaporation of the solvent. This Example resulted in a hydrogenation time of about 71 minutes, a yield of about 89% and a color value of 0.017. The addition of acetic anhydride was begun at about 28% completion of the hydrogenation reaction.

EXAMPLE 8

Example 8 utilizes a process within the scope of this invention.

About 200 g of p-nitrophenol, about 240 g of water, and about 0.8 g of wet palladium on carbon catalyst were charged to a reactor which was then purged of oxygen. Hydrogen was introduced at a pressure of about 70 psig, the reactor was heated to about 50° C., and the heat of the hydrogenation reaction brought the temperature of the reactor up to about 90° C. The reactor was maintained at a constant temperature of about 90° C. After the hydrogenation was approximately 25% complete, a continuous feed of acetic anhydride was initiated. The acetic anhydride was added at a rate such that there was always unreacted p-aminophenol in the reactor. A total of 160 g of acetic anhydride was added. After the addition of the acetic anhydride was complete, the reaction mass was held under constant pressure and temperature for about 60 minutes. After this hold time, the reaction mass was filtered and cooled to produce crystalline N-acetyl-p-aminophenol. The hydrogenation time was about 74 minutes and the color value was 0.028.

COMPARATIVE EXAMPLE F

Comparative Example F which is outside the scope of this invention used the same procedure as Example 11 except that about 200 g of p-nitrophenol and about 245 g of water and no isopropanol were added to the autoclave resulting in about a 45% p-nitrophenol concentration. A 0.1% catalyst loading was used. The acetic anhydride addition was started at about 11 minutes. A total of 161 g of acetic anhydride was added over an 88 minute addition time. The acetic anhydride was added at a rate such that the amount of acetic anhydride in the system exceeded the amount of p-aminophenol in the system during the hydrogenation. This Example resulted in a hydrogenation time of about 102 minutes, a yield of about 86%, and a color value of 0.039. These results compare with a norm of about 80 minutes hydrogenation time or less for a similar system such as Example 8 in which the acetic anhydride is not allowed to reach an excess over the p-aminophenol.

COMPARATIVE EXAMPLE G

Comparative Example G which is outside the scope of this invention used the same procedure as Example 1 except that about 200 g of p-nitrophenol, about 170 g of water and about 75 g of isopropanol were added to the autoclave, resulting in about a 45% p-nitrophenol concentration. A 0.1% catalyst loading was used. The acetic anhydride addition was started at about 20 minutes. A total of about 154 g of acetic anhydride was added over a 31 minute addition time. The acetic anhydride was added at a rate such that the amount of acetic anhydride in the system exceeded the amount of p-aminophenol in the system during the hydrogenation. This Example resulted in a hydrogenation time of about 67 minutes, a yield of about 66%, and a color value of 0.290. These results compare with a norm of about 50 minutes hydrogenation time or less for a similar system, such as Example 3, in which the acetic anhydride is not allowed to reach an excess over the p-aminophenol.

The results of Examples are summarized in the Table below.

| Ex. No. | Process Type | Hydrogenation Time | Yield % | Color Value |
|---|---|---|---|---|
| A | 2-step | 57 mins. | 87.5 | 0.043 |
| B | 2-step | 56 mins. | 80 | 0.029 |
| C | 2-step | 51 mins. | 81 | 0.022 |
| D | 2-step | 62 mins. | 79 | 0.022 |
| E | 2-step | 56 mins. | 85 | 0.033 |
| 1 | Concurrent, no excess acetic anhydride | 61 mins. | 89.5 | 0.013 |
| 2 | Concurrent, no excess acetic anhydride | 50 mins. | 81 | 0.018 |
| 3 | Concurrent, no excess acetic anhydride | 50 mins. | 90 | 0.013 |
| 4 | Concurrent, no excess acetic anhydride | 51 mins. | 88 | 0.020 |
| 5 | Concurrent, no excess acetic anhydride | 80 mins. | 88 | 0.006 |
| 6 | Concurrent, no excess acetic anhydride | 31 mins. | 79 | 0.003 |
| 7 | Concurrent, no excess acetic anhydride | 71 mins. | 89 | 0.011 |
| 8 | Concurrent, no excess acetic anhydride | 74 mins. | — | 0.028 |
| F | Concurrent, with excess acetic anhydride | 102 mins. | 86 | 0.039 |
| G | Concurrent, with excess acetic anhydride | 67 mins. | 66 | 0.290 |

A comparison of Examples 1 through 8 which are within the scope of this invention with Comparative Examples A through E and Comparative Examples F and G shows that the process of this invention produces a product with a marked, unexpected improvement in color value compared to both the two-step reaction and to the coreaction in which there is excess acetic anhydride in the system.

A number of factors must be considered in analyzing the hydrogenation times of the Examples. The hydrogenation time is generally shorter in systems in which isopropanol is present. The hydrogenation time is also affected by the amount of p-nitrophenol charged to the system. As a result, Comparative Examples F and G must be compared to similar systems in order to reach any conclusions. Comparative Example F, with a 102 minute hydrogenation time, can be compared to Example 8, with a 74 minute hydrogenation time. Similarly, Comparative Example G, with a 67 minute hydrogenation time, can be compared with Examples 2, 3, and 4, each of which has a hydrogenation time of about 50 minutes. By these comparisons, it can be seen that an excess of acetic anhydride in the system increases the hydrogenation time, over a system within this invention. In a similar manner, Comparative Examples A-E can be compared with Examples 1, 2, 3, 4, and 6. These comparisons show that the hydrogenation time is not adversely affected by using the process of this invention.

One skilled in the art will recognize many variations in the procedure of this invention described above. It is intended that all variations be within the scope of this invention.

We claim:

1. A process for producing N-acetyl-p-aminophenol comprising:
    (a) providing a quantity of p-nitrophenol;
    (b) first hydrogenating at least 5% of said p-nitrophenol to p-aminophenol; and then (c) continuing said hydrogenating while concurrently acetylating p-aminophenol with acetic anhydride to produce N-acetyl-p-aminophenol;

wherein prior to hydrogenating 80% of said p-nitrophenol the molar concentration of acetic anhydride is not greater than the molar concentration of p-aminophenol.

2. A process according to claim 1 comprising first hydrogenating at least about 20% of said p-nitrophenol to p-aminophenol.

3. A process according to claim 2 comprising first hydrogenating up to about 35% of said p-nitrophenol.

4. A process according to claim 1 wherein said acetylating is by addition of acetic anhydride at a molar rate approximately equal to a molar rate of said hydrogenating.

5. A process according to claim 1 comprising providing said quantity of p-nitrophenol at a concentration between 50% and 80%.

6. A process comprising concurrently hydrogenating p-nitrophenol to p-aminophenol and adding acetic anhydride to acetylate p-aminophenol to N-acetyl-p-aminophenol wherein at least about 80% of said p-nitrophenol is hydrogenated prior to the molar concentration of acetic anhydride exceeding the molar concentration of p-aminophenol.

7. A process according to claim 6 wherein said adding of acetic anhydride is at a molar rate approximately equal to the molar rate of hydrogenating.

8. A process according to claim 6 wherein up to about 35% of p-nirophenol is hydrogenated prior to adding acetic anhydride.

9. A process according to claim 8 wherein at least about 90% of said p-nitrophenol is hydrogenated prior to the molar concentration of acetic anhydride exceeding the molar concentration of p-aminophenol.

10. A process for producing N-acetyl-p-aminophenol comprising
    (a) hydrogenating between 5% and 35% of a quantity of p-nitrophenol to p-aminophenol in the absence of acetic anhydride; and
    (b) concurrently hydrogenating up to about 80% of said quantity of p-nitrophenol and acetylating p-aminophenol by addition of acetic anhydride, wherein said addition of acetic anhydride is at a molar rate approximately equal to the molar rate of hydrogenating.

11. A process according to claim 10 comprising providing said quantity of p-nitrophenol in a concentration between 50% and about 80% in an aqueous medium.

12. A process according to claim 11 comprising providing said quantity of p-nitrophenol in a concentration of at least about 75%.

* * * * *